US009410928B2

(12) United States Patent
Murthy

(10) Patent No.: US 9,410,928 B2
(45) Date of Patent: Aug. 9, 2016

(54) SYSTEM AND METHOD FOR DETECTING METALS IN A SOLUTION

(71) Applicant: ATONARP INC., Minato-ku, Tokyo (JP)

(72) Inventor: Prakash Sreedhar Murthy, Tsukuba (JP)

(73) Assignee: ATONARP INC., Hachioji-Shi, Tokyo (JP)

( * ) Notice: Subject to any disclaimer, the term of this patent is extended or adjusted under 35 U.S.C. 154(b) by 0 days.

(21) Appl. No.: 14/425,225

(22) PCT Filed: Sep. 4, 2013

(86) PCT No.: PCT/JP2013/005227
§ 371 (c)(1),
(2) Date: Mar. 2, 2015

(87) PCT Pub. No.: WO2014/038191
PCT Pub. Date: Mar. 13, 2014

(65) Prior Publication Data
US 2015/0219599 A1    Aug. 6, 2015

(30) Foreign Application Priority Data
Sep. 4, 2012 (JP) ................ 2012-193684

(51) Int. Cl.
*H01J 49/26*    (2006.01)
*G01N 27/62*    (2006.01)

(52) U.S. Cl.
CPC ................. *G01N 27/624* (2013.01)

(58) Field of Classification Search
USPC ................. 250/281, 282, 283, 288
See application file for complete search history.

(56) References Cited

U.S. PATENT DOCUMENTS

2012/0248301 A1*  10/2012  Short ............... H01J 49/147
                                                  250/282
2015/0041641 A1    2/2015  Morokuma et al.

FOREIGN PATENT DOCUMENTS

EP    2 253 952      11/2010
JP    2009-179587 A   8/2009
(Continued)

OTHER PUBLICATIONS

International Preliminary Report on Patentability and Written Opinion of the International Searching Authority (Forms PCT/IB373 and PCT/ISA/237) issued on Mar. 19, 2015, by the International Bureau of WIPO, in corresponding International Application No. PCT/JP2013/005227. (6 pages).

(Continued)

*Primary Examiner* — Nicole Ippolito
(74) *Attorney, Agent, or Firm* — Buchanan Ingersoll & Rooney PC

(57) ABSTRACT

There is provided a system that detects metal ions in a solution easily and with high precision. Such system includes: a unit that produces a mixed solution by mixing a first solution, which includes a first organic compound that has affinity with metal ions to be measured, and a second solution to be measured and supplies the mixed solution to a container; and a unit that detects the metal ions to be measured in the second solution based on a spectrum obtained by ionizing gas in a head space of the container. An example of the first organic compound is siderophores, such as catechol or AHA. The unit that detects the concentration is an ion mobility sensor and is capable of detecting the concentration of metal ions in a solution in real time.

10 Claims, 3 Drawing Sheets

(56) References Cited

FOREIGN PATENT DOCUMENTS

| JP | 2012-104247 A | 5/2012 |
|---|---|---|
| WO | WO 2012/056709 A1 | 5/2012 |

OTHER PUBLICATIONS

International Search Report (PCT/ISA/210) mailed on Nov. 5, 2013, by the Japanese Patent Office as the International Searching Authority for International Application No. PCT/JP2013/005227.
Written Opinion (PCT/ISA/237) mailed on Nov. 5, 2013, by the Japanese Patent Office as the International Searching Authority for International Application No. PCT/JP2013/005227.
Nakashima et al, "Rapid Spectrophotometric Determination of Trace Iron in Boiler Water", Journal of Japan Society for Analytical Chemistry, 1962, vol. 11, No. 1, pp. 73 to 77.
Supplementary European Search Report issued in corresponding European Patent Application No. 13835276.0-1554/2894468 PCT/JP2013/005227, dated May 10, 2016 (12 pages).
Parvin Shahdousti et al. Headspace-solid phase microextraction of selenium(IV) from human blood and water samples using polypyrrole film and analysis with ion mobility spectrometry, Analytica Chimica Acta, Elsevier, Amsterdam, NL, vol. 684, No. 1-2, Jan. 17, 2011, pp. 67-71.
Marilyn S. Black, "Volatile Metal-Chelate Sample Introduction for Inductively Coupled Plasma-Atomic Emission Spectrometry", Analytical Chemistry, American Chemical Society, vol. 53, No. 2, Feb. 1981, pp. 249-253.
Database WPI, Week 200912, 2009, Thomson Scientific, London, GB; AN 2009-E24910, XP002756874, CN 101339126 Abstract, Jan. 7, 2009.
Sanna Holopainen et al., "Sample-extraction methods for ion-mobility spectrometry in water analysis", Trends in Analytical Chemistry, vol. 37, 2012, pp. 124-134.
Edra Dodbiba et al., "Sensitive analysis of metal cations in positive ion mode electrospray ionization mass spectrometry using commercial chelating agents and cationic ion-pairing reagents", Rapid Communications in Mass Spectrometry, vol. 25, No. 9, Mar. 19, 2012, pp. 1005-1013.

\* cited by examiner

SYSTEM AND METHOD FOR DETECTING METALS IN A SOLUTION

TECHNICAL FIELD

The present invention relates to a system and method for detecting metals in a solution.

BACKGROUND ART

Japanese Laid-Open Patent Publication No. 2009-179587 discloses the provision of a siderophore that has a favorable binding ability with iron ions and helps iron ions have a stable presence in an aqueous solution and a marine environment modifier that includes such siderophore.

PCT publication WO2012/056709 discloses a system with a unit for analyzing samples that was proposed by the present applicant. The unit for analyzing includes: a functional unit that detects peaks that are present in a two-dimensional representation of data included in measurement data obtained by feeding a sample to an ion mobility sensor for measuring the ionic strength of ionized chemical substances that pass through an electric field controlled by at least two parameters, the two-dimensional representation indicating the ionic strength when a first parameter has been changed and the other parameter is fixed; a functional unit that classifies the peaks detected on the basis of the continuity between and the birth and death of the detected peaks and the other peaks that are present in the two-dimensional representation; and a functional unit that estimates the chemical substances contained in the sample on the basis of the classified peaks.

DISCLOSURE OF THE INVENTION

There is demand for a simple method of measuring (analyzing) minute amounts of metal ions in liquids and solids. Although ICP-MS is known as a method of analyzing metal ions, such equipment is expensive and has a high running cost.

One aspect of the present invention is a system including: a unit that supplies a mixed solution produced by mixing a first solution, which includes a first organic compound that has affinity with metal ions (a species of metal ions) to be measured, and a second solution to be measured to a container; and a unit that detects the metal ions to be measured in the second solution based on a spectrum obtained by ionizing components in a gas in a head space of the container.

The inventors of the present application found out that the spectrum obtained by ionizing components in gas in a head space changes when the concentration of metal ions in a solution including the first organic compound is changed. For example, peaks that increase or decrease, or conversely decrease and increase, in relation to an increase or decrease in the concentration of metal ions to be measured in the second solution are found out in a spectrum measured by ionizing the components in gas in the head space.

In the present system, metal ions in a solution (in the second solution) are mixed with the first solution and are trapped by the first organic compound, and by ionizing the components in the gas in the head space, it is possible to detect the metal ions in the solution. According to the present system, it is possible to detect metal ions in a solution at low cost, with a simple configuration, and also in real time without needing to vaporize metal ions in the solution at high temperature, using high energy to directly ionize the metal ions in the solution, causing a phase change in the solution itself, or carrying out multiple ionization using an ICP-MS for example while consuming a large amount of argon gas. In addition, by carrying out calibration in advance for the relationship between the peak components included in the spectrum measured by ionizing the components in the gas in the head space and the concentration of the metal ions to be measured included in the second solution, it is possible to measure the presence and amount of the metal ions to be measured in the second solution with high precision.

The unit that supplies may include a mixing unit that produces a flow of the mixed solution in which a flow of the first solution and a flow of the second solution are mixed, the container may include a part where the mixed solution flows, and the unit that detects may include a unit that detects the metal ions to be measured in the flow of the second solution based on a spectrum measured by ionizing components of a gas in the head space to the part where the mixed solution flows. It is possible to detect fluctuations over time in the metal ions to be measured included in the second solution. In addition, in the case where the unit that detects concentration is a real time sensor such as an ion mobility sensor, it is possible to measure and analyze fluctuations in the metal ions to be measured included in the second solution in real time.

It is desirable for the present system to further include a unit that changes the concentration of the first organic compound in the first solution and/or the concentration of the first organic compound in the mixed solution according to a state of the spectrum. The detection sensitivity of metal ions to be measured in the mixed solution depends on the concentration of the first organic compound in the mixed solution. Accordingly, it is desirable to control the concentration of the first organic compound in order to control the dynamic range of the system and make adjustments in response to the peaks included in a spectrum being too small or too large.

A typical example of the first organic compound is organic matter or a protein that adjusts the concentration of metal ions and/or collects metal ions in an organism. A typical example of organic matter that collects metal ions is a siderophore. The system may further include a unit that supplies to a unit that produces the first solution that includes siderophore. In the case where the metal ions to be measured are iron ions, a typical example of the siderophore is catechol (CTC) or AHA (Acetohydroxamic acid or Lithostat).

Another aspect of the present invention is a method including detecting metal in a solution. Detecting metal in the solution includes the steps below.

1. Producing a mixed solution by mixing a first solution, which includes a first organic compound that has affinity with metal ions to be measured, and a second solution to be measured.
2. Detecting the metal ions to be measured in the second solution based on a spectrum obtained by ionizing components in a gas in a head space of a container including or holding the mixed solution.

The detecting the metal in a solution may include generating a flow of the mixed solution and a spectrum is acquired by ionizing the gas in the head space of a part where the mixed solution flows. It is possible to detect metal ions to be measured included in the flow of the second solution based on a spectrum measured by ionizing components in the gas of the first organic compound in the head space of the part (flow path) of the container where flowing occurs. The detecting metal in a solution may include changing at least one of the concentration of the first organic compound in the first solution and the concentration of the first organic compound in the mixed solution according to the state of the spectrum. By controlling the concentration of the first organic compound according to the concentration of the metal ions to be measured included in the second solution, it is possible to adjust the measurement sensitivity.

A typical example of the first organic compound is a siderophore and it is effective to include supplying a first solution that includes a siderophore. An example of a siderophore is catechol or AHA.

This method may include generating the second solution by dissolving a solid to be measured. If the substance to be measured is a solid and such solid is dissolved and the metal in the solid is converted to metal ions in the solution, it will be possible to carry out measurement in the same way as described above. In addition, by carrying out calibration in advance for the relationship between the peak components in the obtained spectrum and the concentration of metal ions to be measured included in the second solution, it is possible to measure the presence and/or amount of metal to be measured in a solution and in a solid.

DETAIL DESCRIPTION

Figure 1:
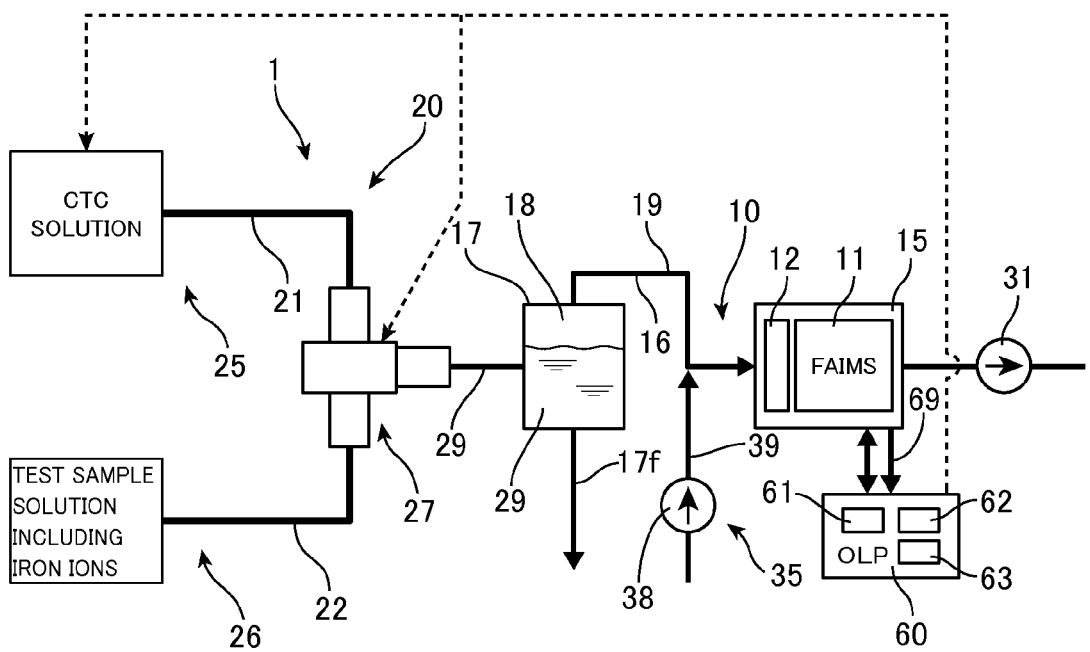
FIG. 1 is a block diagram showing the overall configuration of a metal detecting system.

FIG. 1 shows an overview of a metal detecting system equipped with an ion mobility sensor. One example of an ion mobility sensor 11 is a FAIMS (Field Asymmetric waveform Ion Mobility Spectrometry, field asymmetric waveform ion mobility spectrometer), or DIMS (Differential Ion Mobility Spectrometry). The sensor 11 may be a sensor that obtains a spectrum by ionizing components (gases) in air, or may be a mass spectrometer, gas chromatography, or the like.

With FAIMS (FAIMS technology), the chemical substance to be measured is a compound, composition, molecule, or other product that can be ionized by an ionization unit 12 disposed upstream of the FAIMS 11. FAIMS uses a property whereby ion mobility is unique for each chemical substance and applies a differential voltage (DV, Dispersion Voltage, Vd voltage, field voltage, AC voltage, hereinafter "Vf") and a compensation voltage (CV, compensation voltage, DC voltage, hereinafter "Vc") while causing a substance to move in an electric field. By appropriately controlling the values of Vf and Vc, an ionized chemical substance that is the detection target will reach a detection electrode and be detected as a current value.

This metal detecting system 1 includes a unit (mixed solution producing unit) 20 that produces a mixed solution 29, in which a first solution containing an first organic compound that has affinity for the metal ions (a specific metal ions or a species of metal ions) to be measured and a second solution to be measured are mixed, and supplies the mixed solution 29 to a container (reservoir) 17, a unit (detection unit) 10 that detects the concentration of the first organic compound in a head space 18 of the reservoir 17 in which the mixed solution 29 is present, a system (carrier gas supplying system) 35 that supplies a carrier gas 39, and an intake pump 31. The carrier gas supplying system 35 includes a blower (fan) 38 that supplies air (dry air) as the carrier gas 39.

The mixed solution producing unit 20 includes a first supplying unit 25 that supplies a first solution 21 including catechol (CTC) that is the first organic compound (first organic composition), a second supplying unit 26 that supplies a second solution 22 that is to be measured, and a mixer 27 that mixes the first solution 21 and the second solution 22 to produce the mixed solution 29. The first supplying unit 25 continuously supplies a predetermined amount of the first solution (a flow of the first solution) 21 to the mixer 27 and the second supplying unit 26 continuously supplies a predetermined amount of the second solution (a flow of the second solution) 22 to the mixer 27. The mixer 27 produces the mixed solution (a flow of mixed solution) 29 in which the first solution 21 and the second solution 22 have been mixed with predetermined proportions and supplies the mixed solution 29 to the reservoir 17. The second solution 22 may be such as the feed water of a power station, drinking water, discharge water, waste water and the like.

The reservoir 17 includes a flush line 17f and the mixed solution 29 flows inside the reservoir 17. Inside the reservoir 17, the head space 18 for a gas layer is formed above the liquid layer of the mixed solution 29 that passes through the reservoir 17. The mixed solution 29 stays in the reservoir 17 for a predetermined time to form an equilibrium state with the head space 18 and after that is discharged using the flush line 17f.

The detection unit 10 includes a sensor unit 15, a pipe 16 that supplies the gas (sample gas) 19 in the head space 18 to the sensor unit 15, and a control device (olfaction processor, OLP) 60. The sample gas 19 is supplied to the sensor unit 15 having been mixed with the carrier gas 39. One example of the carrier gas 39 is air, with dry air being desirable.

The sensor unit 15 includes the FAIMS 11 and the ionizing unit 12 that ionizes the chemical components (molecules) included in the sample gas 19 upstream of the FAIMS 11. One example of the FAIMS 11 is a MEMS sensor provided by Owlstone. One example of the ionizing unit 12 ionizes a gas using UV (ultra-violet). The ionizing unit 12 may be an ionizer that uses $Ni_{63}$ (a 555 MBq β-ray source, 0.1 μSv/hr) or may be an ionizer that uses corona discharge. The ionizing unit 12 in the present embodiment includes a UV source such as a UV light emitting diode (UV-LED) or a UV lamp (UV low pressure lamp), and ionizes components included in the carrier gas 39 by emitting light of a short wavelength of 280 nm or below.

The control device (OLP) 60 includes a function (functional unit) 61 that controls the state (measurement conditions or environment) of the system, such as the flow rate passing the FAIMS 11, a function (detection function, functional unit) 62 that detects metal ions to be measured (in the present embodiment, iron ions) present in the second solution 22 based on measurement data (spectra, IMS data) 69 obtained from the FAIMS 11, and a function (concentration adjustment function, functional unit) 63 that changes the concentration of the first organic compound included in the mixed solution 29 based on the obtained IMS data. 69.

The detection function 62 may include a function of measuring the presence and/or contained amount of iron ions in the second solution 22. By carrying out calibration (characterization) in advance of the relationship among the profile of the peaks included in the IMS data 69 measured by ionizing the gas in the head space 18, the conditions of the first solution 21, such as the concentration of catechol, and the iron ion concentration to be measured included in the second solution 22, it is possible to find the iron ion concentration of the solution 22 based on the IMS data 69.

The concentration adjustment function 63 controls the supplying unit 25 to control the concentration of the first organic compound (first organic composition), such as CTC, included in the first solution 21 and also adjusts the concentration of the first organic compound included in the mixed solution 29 by controlling the mixing ratio of the mixer 27. If the peaks included in the IMS data 69 exceed the measurement range or the peaks are too small and the measurement precision is low, by controlling the concentration of the first organic compound included in the mixed solution 29, it is possible to set conditions that are suited to quantitative analysis.

The OLP 60 may be realized by general-purpose hardware resources (including a CPU and memory) of a personal computer or the like or may be provided as a single integrated device (semiconductor chip, ASIC, LSI) or a plurality of integrated chips (a chip set). The function 61 of the OLP 60 that controls the FAIMS 11 includes a function of analyzing (interpreting) the measurement results according to measurement conditions or the environment.

This metal detecting system 1 has an object of detecting iron ions in the second solution (sample solution) 22. Iron (Fe) has a boiling point of at least 2860° C. and a first ionization energy of 659 KJ/mol (around 8.2 eV), is present in a solution (for example, in water) as divalent (ferrous) or trivalent (ferric) iron ions, and reacts with water to become ionized, especially at high temperature. The detection of iron ions in a solution is carried out with objects such as monitoring the state of a plant, monitoring the water quality of waste water, and maintaining the water quality of drinking water. However, a system for monitoring continuously or in real time has fundamentally not been provided, and in particular a system that detects the presence of iron ions with a concentration of ppm or below, for example at ppb level, is yet to be provided.

The metal detecting system 1 supplies the first solution 21 including CTC as the first organic compound that has affinity with the iron ions to be measured. CTC (catechol, $C_6H_6O_2$) is a siderophore that is water soluble and is a carrier of iron ions. CTC binds with (ferric) iron ions in a solution to form a catecholate-iron complex. Hydroxamic acid (R—C(=O)—NH—OH), compounds including carboxylate (hydroxy-carboxic acids, for example, derivatives of citric acid, with citric acid also functioning as a siderophore), and acetohydroxamic acid (AHA, Lithostat, $C_2H_5NO_2$) can also be given as other examples of a siderophore that forms a chelate complex with iron ions. AHA and CTC have hexadentate ligand structure, and their binding sites are occupied by the six coordination sites of the metal to form chelate bonds with the iron ions. Although such siderophores are examples that are included in microorganisms, bacteria and the like, the siderophore included in the present specification are not limited to those mentioned above.

Siderophores that generate a chelate complex with metal ions other than iron and function as metal-collecting organic matter (metal-collecting proteins) are also known. For example, desferrioxamine-B (DFOB) can be given as a siderophore that has high binding force with uranium and functions as metal-collecting organic matter for uranium. Siderophores that respectively bind with metal ions of aluminum, gallium, chromium, copper, zinc, lead, magnesium, cadmium, vanadium, indium, plutonium, and the like are known. When measuring such metal ions present in a solution, it is possible to employ a system and method that use a siderophore with high affinity for a specific metal ions to be measured in place of the CTC or AHA described below.

Figure 2:
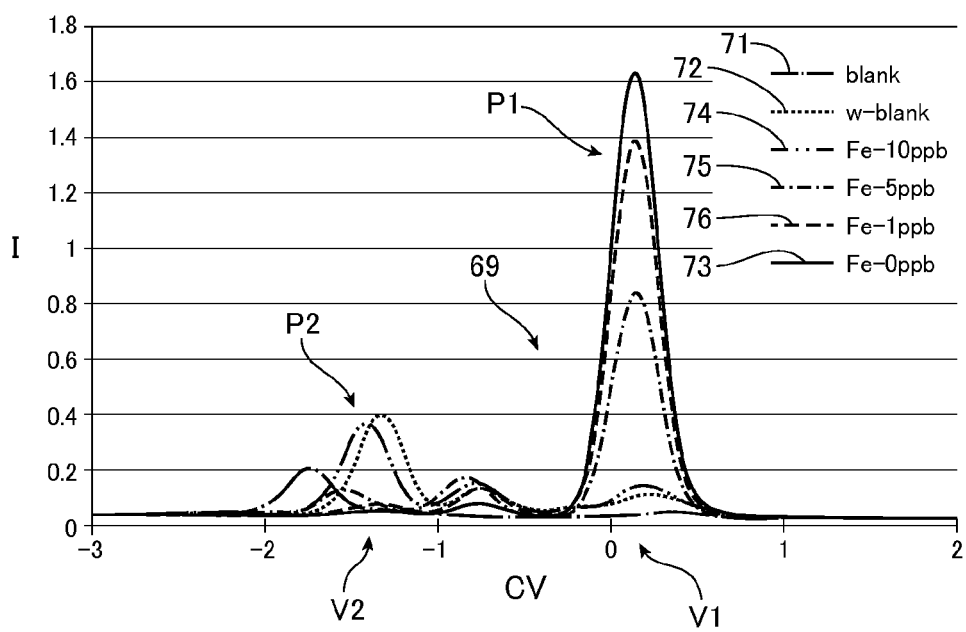
FIG. 2 is a graph showing an example where iron ions have been detected using CTC.

FIG. 2 shows an example where metal ions (iron ions) are detected using CTC as the first organic compound. In this example, the mixed solution 29 where 0 to 10 ppb of iron ions are included in a CTC solution (80° C., 100 ppm) is introduced into the reservoir 17, 80° C. is maintained, and gas 19 sampled from the head space 18 is measured by the FAIMS 11. The vertical axis shows the ion current (I) and the horizontal axis shows the compensation voltage (CV(V)). FIG. 2 shows the measurement results for plus ions when the DV is 68%.

The first graph 71 shows the results produced when the background (carrier gas) was measured, and the second graph 72 shows the results of measuring the sample gas (which hereinafter includes the carrier gas) 19 collected or sampled from the head space 18 when only water was supplied. The third graph 73 shows the results of measuring the sample gas 19 when a CTC (100 ppm) aqueous solution (the first solution 21) was supplied. The fourth graph 74 shows the results of measuring the sample gas 19 when the mixed solution 29, where 10 ppb of iron ions are included in the CTC aqueous solution, was supplied. The fifth graph 75 shows the results of measuring the sample gas 19 when the mixed solution 29, where 5 ppb of iron ions are included in the CTC aqueous solution, was supplied. The sixth graph 76 shows the results of measuring the sample gas 19 when the mixed solution 29, where 1 ppb of iron ions are included in the CTC aqueous solution, was supplied.

As is understood from the third graph 73 in FIG. 2, a peak P1, which is assumed to be the CTC migrating into the head space 18, appears when the CV value of the IMS data (spectrum) 69 is in the vicinity of V1. The peak P1 is assumed to be caused by CTC that has evaporated (migrated) from the mixed solution 29 and the first solution 21 into the head space 18 and detected by the FAIMS 11, and is to be a physical amount that is proportionate to, or related to using an appropriate function, the concentration of the CTC in the head space 18.

The height of the peak P1 falls as the amount of iron ions included in the mixed solution 29 increases, and it is understood that the amount of CTC present in the head space 18 changes (falls) corresponding to the amount of iron ions included in the mixed solution 29. By analyzing the gas in the head space 18 using the FAIMS 11 and measuring the amount (concentration) of CTC present in the head space 18, it comes to find that it is possible to detect the amount (concentration) of iron ions included in the mixed solution 29 at, at least a ppb level.

If the head space 18 and the mixed solution 29 are in an equilibrium state via the liquid surface inside the reservoir 17, it is assumed that the concentration of CTC of the head space 18 will be proportionate to or correspond to the concentration of the CTC in the mixed solution 29 and it shows that the concentration of CTC in the mixed solution 29 will have fallen due to an increase in iron ions in the mixed solution 29. Accordingly, by using the system (measuring apparatus, detecting apparatus) 1, it is possible to detect a rise and fall of the iron ion concentration in the mixed solution 29 and the second solution 22 at a ppb level according to a rise or fall in the concentration of CTC in the head space 18. Also, by carrying out calibration in advance for the iron ion concentration in the mixed solution 29 and the height of the peak P1, it is possible to determine the iron ion concentration in the mixed solution 29, and possible to determine the ion concentration in the second solution 22 from the mixing ratio of the first solution 21 and the second solution 22.

Also, a peak P2 where there is a tendency for the height to increase as the amount of iron ions included in the mixed solution 29 increases appears when the CV value of the IMS data 69 is in the vicinity of V2. Accordingly, molecules whose presence in the head space 18 increases corresponding to the amount of iron ions included in the mixed solution 29 are detected. It is believed that this corresponds to the catechol iron complex migrating (evaporating) into the head space 18. Accordingly, it is possible to detect the amount (concentration) of iron ions included in the mixed solution 29 from the height of the peak P2 at, at least a ppb level.

Such IMS data 69 is data that can be acquired in real time from the FAIMS 11. Accordingly, by analyzing the IMS data 69, it is possible to detect the concentration of iron ions in a solution extremely simply, in real time, and with high precision by individually or collectively analyzing a number of elements (peaks).

The dynamic range for detecting the iron ions in the system 1 also depends on the CTC concentration in the mixed solution 29. Accordingly, if the height of a peak included in the IMS data 69 is saturated or the peak is too low and sufficient precision is not obtained, the concentration adjustment function 63 of the OLP 60 controls the first supplying unit 25 to adjust the concentration of CTC in the first solution 21 and/or controls the mixer 27 to adjust the mixing ratio of the first solution 21 and the second solution 22. According to this control, it is possible to maintain a state where the state of the IMS data 69 is suited to quantitative analysis.

Figure 3:
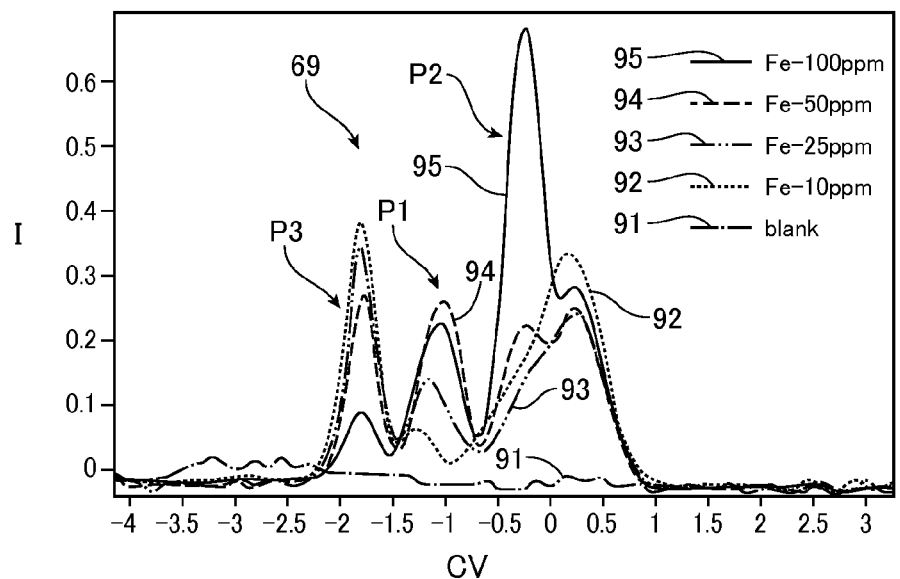
FIG. 3 is a graph showing an example where iron ions have been detected using AHA.

FIG. 3 shows an example where metal ions (iron ions) are detected using AHA as the first organic compound. In this example, the mixed solution 29 where 10 to 100 ppm of iron ions are included in an AHA solution (80° C., 100 ppm) is introduced into the reservoir 17, 80° C. is maintained, and gas 19 sampled from the head space 18 is measured by the FAIMS 11. The vertical axis shows the ion current (I) and the horizontal axis shows the compensation voltage (CV(V)). FIG. 3 shows the measurement result of the FAIMS 11 for plus ions and the DV of the FAIMS 11 is 68%.

The first graph 91 shows the results produced when the background (carrier gas) was measured (blank), and the second graph 92 shows the results of measuring the sample gas 19 when a mixed solution 29 where 10 ppm of iron ions are included in the AHA aqueous solution was supplied. The third graph 93 shows the results of measuring the sample gas 19 when a mixed solution 29 where 25 ppm of iron ions are included in the AHA aqueous solution was supplied. The fourth graph 94 shows the results of measuring the sample gas 19 when a mixed solution 29 where 50 ppm of iron ions are included in the AHA aqueous solution was supplied. The fifth graph 95 shows the results of measuring the sample gas 19 when a mixed solution 29 where 100 ppm of iron ions are included in the AHA aqueous solution was supplied.

A number of peaks are included in the IMS data 69 and a tendency is observed where for the peaks P1 and P2, the peak height increases with an increase in the iron ion concentration, while for the peak P3, the peak height decreases with an increase in the iron ion concentration.

Figure 4:
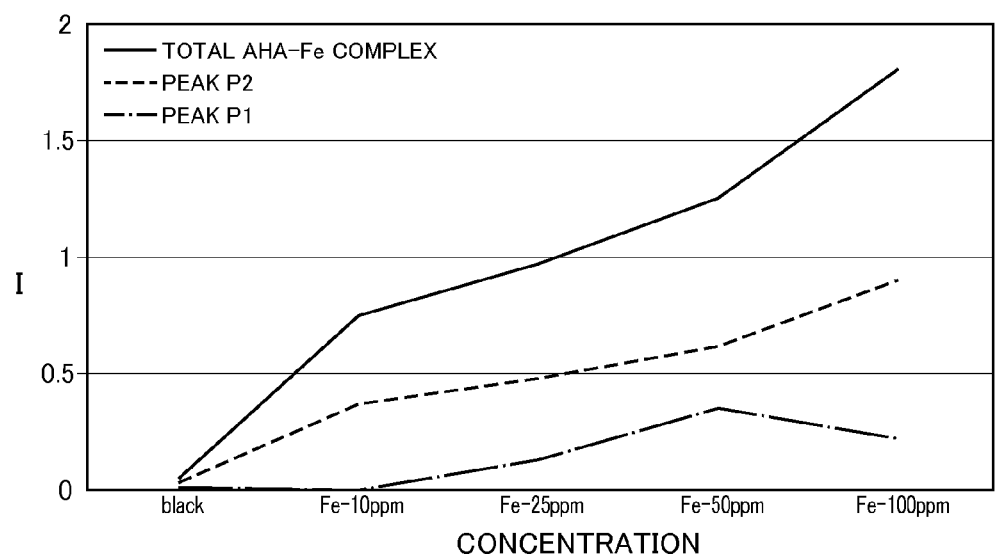
FIG. 4 is a graph showing the characteristics of a spectrum relative to the concentration of iron ions.

FIG. 4 shows the relationship between the peak height and the iron ion concentration. In this IMS data 69, it is understood that a value produced by adding all of the peaks (total AHA-FE complex) is an index that is suited to quantitative analysis of the iron ion concentration. Accordingly, even with an iron ion concentration of the order of ppm, by using the system 1, it is possible to measure the concentration of iron ions in a solution easily, precisely, and in real time.

In this way, using the metal detecting system 1, it is possible to carry out quantitative analysis of metal, which is iron in this example, in an aqueous solution. Quantitative analysis of metals is not easy even with ICP-MS (Inductively Coupled Plasma Mass Spectrometer) and detection in real time is impossible. In addition, since an ICP-MS consumes several hundred liters of argon, the running cost required for measurement is extremely high. In the metal detecting system 1, by using a FAIMS 11 that is capable of detecting molecules in air in real time, it is possible to carry out highly precise measurement at ppb level at low cost and in real time using air as a carrier gas and without using high-cost argon gas or the like.

In addition, the metal detecting system 1 is capable of measuring the metal concentration in an aqueous solution at room temperature or another appropriate temperature that is suited to sampling, with the sample in its present state and without boiling or causing a phase change. This means that it is possible to detect the metal concentration in a solution in the state for which measurement is desired, and energy for causing a phase change of a large amount of the solution or directly ionizing metal such as iron is unnecessary, which makes it possible to detect metal in solution at low cost. Also, by using a substance that is suited to a specific or a species of metal ions to be measured as the siderophore for measurement, it is possible to measure other metal ions in parallel in real time, and it is possible to measure a variety of metal ions included in an aqueous solution at low cost and with high precision.

Figure 5:
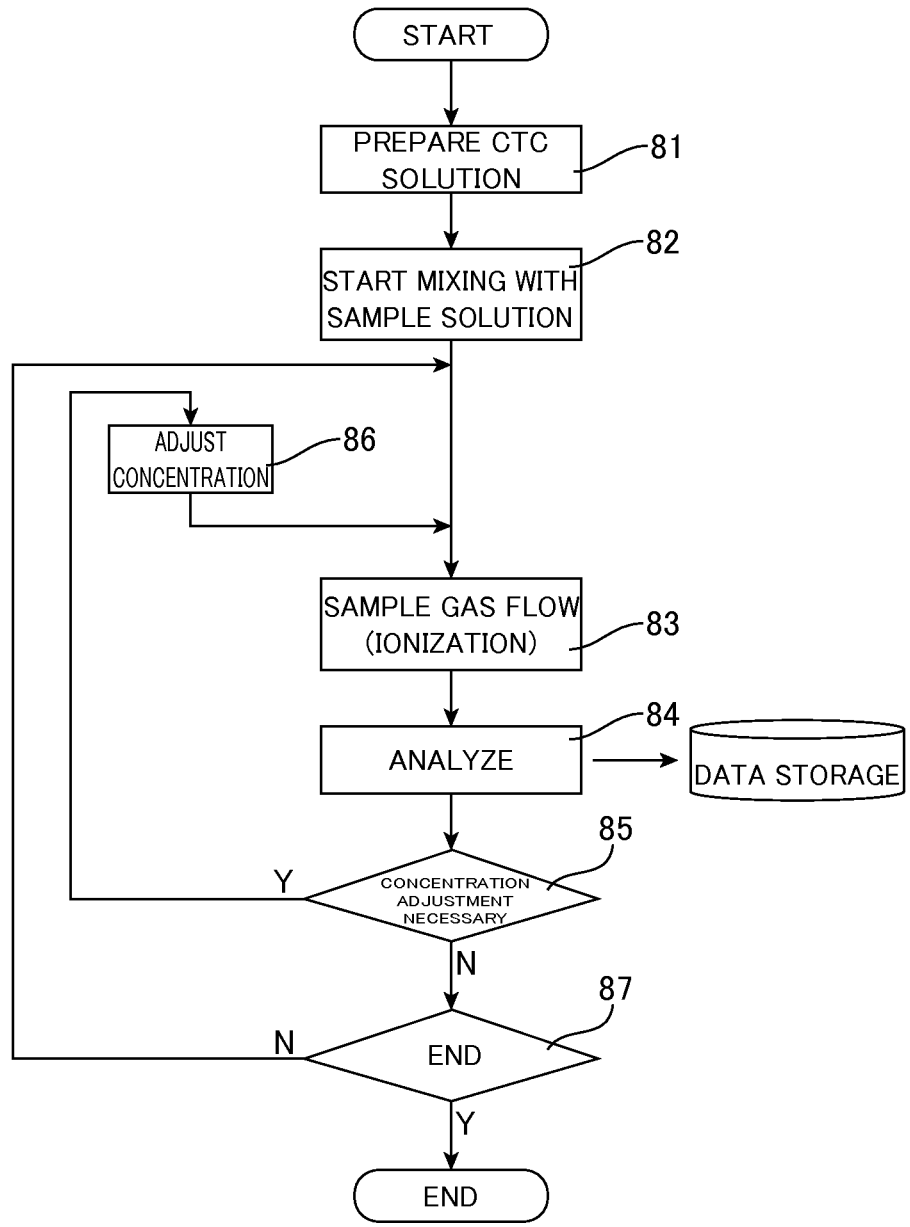
FIG. 5 is a flowchart showing a process of detecting a metal in a solution using the metal detecting system.

FIG. 5 shows a process for detecting metal using the metal detecting system 1 by way of a flowchart. The process shown in the flowchart is also a method of measuring metal ions and is also control method of the metal detecting system 1. As examples, the control method is recorded on an appropriate recording medium as a program (program product) that controls the OLP 60 or is provided via a network.

In step 81, CTC is mixed with pure water to prepare the first solution 21 including CTC with a predetermined concentration. The siderophore is not limited to CTC as described above. To control the sensitivity of the system 1, it is effective to prepared first solutions 21 with a plurality of concentrations. It is also effective to equip the system 1 with a unit that is capable of dynamically adjusting the concentration of the CTC using a high-performance injection pump or the like.

In step 82, the mixing of the first solution 21 and the sample solution (sample water, second solution to be measured) 22 starts. If the substance to be measured is not a liquid and is a solid (including a powder or the like), the sample solution 22 may be a solution in which the solid to be measured is dissolved and step 82 includes a process of dissolving the solid to be measured to produce the second solution 22. Also, in cases where it is difficult to maintain sufficient flow in the pipes, such as where the liquid to be measured has a high concentration or is highly viscose, it is possible to adjust the concentration, the viscosity, or the like using an appropriate solvent.

Once the mixed solution 29 has been prepared, in step 83 the sample gas 19 is collected from the head space 18 and supplied to the sensor unit 15, the components included in the sample gas 19 are ionized, and the IMS data (spectra) 69 is acquired. That is, the metal ions included in the second solution 22 are trapped in the siderophore, such as CTC and by ionizing the gas in the head space 18 at such time, the presence and concentration of metal ions in the second solution 22 or the mixed solution 29 are detected.

In step 84, the IMS data 69 is analyzed, the concentration of metal ions included in the sample solution 22 is calculated from the concentration of metal ions (the concentration of iron ions) included in the mixed solution 29 and the fluctuations in the concentration in the mixed solution 29, and as necessary the results are accumulated in data storage. As one example, it is possible to focus on the peak that reflects the concentration of CTC in the head space 18 from the IMS data 69 and find the iron ion concentration from the behavior or variation in such concentration, and in such case, the peak height and the iron ion concentration are inverted. It is also possible to focus on a peak that reflects the concentration of a matrix of iron ions and CTC in the head space 18 and to find the iron ion concentration from the variation or fluctuations in such concentration, and in such case, the increase/decrease in the peak height and the increase/decrease in the iron ion concentration will match. It is also possible to find the iron ion concentration including other information relating to the IMS data 69, such as the total of the peak height, area, and peak positions.

In step 85, if it is determined that highly precise information on the iron ion concentration has not been obtained from the IMS data 69, in step 86, concentration adjustment is carried out to adjust the CTC concentration of the first solution 21, to adjust the mixing ratio of the first solution 21 and the second solution 22, and/or to adjust the concentration of the second solution 22.

The processes described above are repeated until analysis of metal ions in the sample solution 22 ends in step 87. As one example, by sampling water supply and drainage and circulating water during the operation of a plant and carrying out analysis by repeating such processes on such water samples, it is possible to continuously monitor the operating conditions of a plant in real time.

Note that although the metal detecting system 1 described above uses the FAIMS 11 to analyze the sample gas 19, the sensor may be an ion mobility sensor of another type or may be an analyzer that detects an ionized component, such as a mass spectrometer. However, since it is possible for an ion mobility sensor to measure components (molecules) in air, this is favorable for a low-cost metal detecting system that is easy to manage. Although a liquid surface is produced inside the reservoir to maintain a head space in the metal detecting system 1 described above, it is also possible to place the mixed solution in contact with a diffusive or permeable porous membrane and form the head space via such membrane, with the method of forming the head space not being limited to such methods.

The invention claimed is:

1. A system comprising:
a unit that supplies a mixed solution produced by mixing a first solution that includes a first organic compound that has affinity with metal ions to be measured, and a second solution to be measured to a container;
a unit that detects the metal ions to be measured in the second solution based on a spectrum obtained by ionizing gas in a head space of the container; and
a unit that changes at least one of a concentration of the first organic compound in the first solution and a concentration of the first organic compound in the mixed solution according to a state of the spectrum.

2. The system according to claim 1,
wherein the unit that supplies includes a mixing unit that produces a flow of the mixed solution in which a flow of the first solution and a flow of the second solution are mixed,
the container includes a part where the mixed solution flows, and
the unit that detects includes a unit that detects the metal ions to be measured in the flow of the second solution based on a spectrum obtained by ionizing gas in the head space to the part where the mixed solution flows.

3. The system according to claim 1, wherein the first organic compound includes a siderophore.

4. The system according to claim 3, wherein the siderophore is catechol or AHA.

5. The system according to claim 1, wherein the unit that detects includes an ion mobility sensor.

6. A method including detecting metal in a solution,
wherein detecting metal in the solution comprises:
producing a mixed solution by mixing a first solution that includes a first organic compound that has affinity with metal ions to be measured, and a second solution to be measured;
detecting the metal ions to be measured in the second solution based on a spectrum obtained by ionizing components in a gas in a head space of a container holding the mixed solution; and
changing at least one of a concentration of the first organic compound in the first solution and a concentration of the first organic compound in the mixed solution according to a state of the spectrum.

7. The method according to claim 6,
wherein the producing includes producing a flow of the mixed solution in which a flow of the first solution and a flow of the second solution are mixed and supplying the flow of mixed solution to the container,
the detecting includes detecting the metal ions to be measured in the flow of the second solution based on a spectrum obtained by ionizing components in a gas in the head space to a part of the container where the mixed solution flows.

8. The method according to claim 6,
wherein the first organic compound includes a siderophore.

9. The method according to claim 8, wherein the siderophore is catechol or AHA.

10. The method according to claim 6,
further comprising producing the second solution by dissolving a solid to be measured.

* * * * *